United States Patent
Hossainy

(10) Patent No.: US 7,858,143 B2
(45) Date of Patent: Dec. 28, 2010

(54) APPARATUS AND METHOD FOR COATING STENTS

(75) Inventor: Syed F. A. Hossainy, Fremont, CA (US)

(73) Assignee: Abbott Cardiovascular System Inc., Santa Clara, CA (US)

(*) Notice: Subject to any disclaimer, the term of this patent is extended or adjusted under 35 U.S.C. 154(b) by 904 days.

(21) Appl. No.: 11/800,951

(22) Filed: May 7, 2007

(65) Prior Publication Data

US 2007/0275175 A1  Nov. 29, 2007

Related U.S. Application Data

(63) Continuation-in-part of application No. 10/099,101, filed on Mar. 15, 2002, now Pat. No. 7,232,490.

(51) Int. Cl.
  *B05C 13/00* (2006.01)
  *B05D 3/12* (2006.01)
  *A61L 33/00* (2006.01)

(52) U.S. Cl. .................. 427/2.24; 427/2.1; 427/2.25; 118/500

(58) Field of Classification Search .......... 118/500; 427/2.1, 2.24, 2.25
See application file for complete search history.

(56) References Cited

U.S. PATENT DOCUMENTS

| | | |
|---|---|---|
| 3,067,948 A | 12/1962 | Lang et al. |
| 3,645,447 A | 2/1972 | Cowan |
| 4,733,665 A | 3/1988 | Palmaz |
| 4,776,990 A | 10/1988 | Verity |
| 4,800,882 A | 1/1989 | Gianturco |
| 4,802,627 A | 2/1989 | Moy et al. |
| 4,886,062 A | 12/1989 | Wiktor |
| 5,437,726 A | 8/1995 | Proto et al. |
| 5,514,214 A | 5/1996 | Joel et al. |
| 5,935,135 A * | 8/1999 | Bramfitt et al. ............ 623/1.11 |
| 6,056,993 A | 5/2000 | Leidner et al. |
| 6,167,318 A | 12/2000 | Kizer et al. |
| 6,214,115 B1 * | 4/2001 | Taylor et al. ............... 118/423 |
| 6,527,863 B1 | 3/2003 | Pacetti et al. |
| 6,562,136 B1 * | 5/2003 | Chappa et al. ............. 118/500 |
| 6,682,771 B2 | 1/2004 | Zhong et al. |
| 6,709,514 B1 * | 3/2004 | Hossainy ..................... 118/52 |
| 6,743,462 B1 | 6/2004 | Pacetti |
| 7,211,150 B1 * | 5/2007 | Kokish et al. .............. 118/500 |
| 2008/0280025 A1 * | 11/2008 | Scheer ...................... 427/2.24 |

* cited by examiner

*Primary Examiner*—Timothy H Meeks
*Assistant Examiner*—Cachet I Sellman
(74) *Attorney, Agent, or Firm*—Squire, Sanders & Dempsey L.L.P.

(57) ABSTRACT

An apparatus for coating stents and a method of using the same is provided. The apparatus includes a first stent support and a second stent support for supporting stents. The first and second stent supports are positioned with respect to one another in an adjacent serial configuration such that one end of the first stent support extends from an end of the adjacent second stent support. A motor can be coupled to the first stent support to rotate the first stent support such that the rotation of the first stent support rotates the second stent support. The apparatus further includes an applicator for applying a coating composition to the stents.

10 Claims, 3 Drawing Sheets

APPARATUS AND METHOD FOR COATING STENTS

CROSS REFERENCE

This application is a continuation-in-part of application Ser. No. 10/099,101 which was filed on Mar. 15, 2002, now U.S. Pat. No. 7,232,490.

TECHNICAL FIELD

This invention relates to stent coating systems and methods of coating stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giant-urco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

During the coating process, the therapeutic substance may be exposed to light, thereby damaging the therapeutic substance should the substance be photosensitive. Accordingly, a new apparatus and method for coating stents is needed for protection of the therapeutic substance. Additionally, it is also desirable that the apparatus be able to coat a large number of stents at one time, thereby increasing the manufacturing time of drug-eluting stents.

SUMMARY

In accordance with one aspect of the invention, a method of coating stents is disclosed. In some embodiments, the method comprises placing stents in a coating chamber housing a first stent support and a second stent support for supporting stents. The first and second stent supports are positioned with respect to one another in an adjacent serial configuration such that one end of the first stent support extends from an end of the adjacent second stent support. The method further comprises using a motor coupled to the first stent support to rotate the first stent support such that the rotation of the first stent support causes the second stent support to rotate; and applying a coating composition on the stents by a coating applicator.

The first stent support and the second stent support can rotate at the same rotational speed (or rpm) or different rotational speeds.

A blower can be used to blow or direct warm or cold gas onto the stents. The stents can be positioned vertically in the coating chamber. Alternatively, the stents are positioned horizontally in the coating chamber. A second motor can be used for traversing the stents linearly passed the coating applicator and blower. The coating applicator can be a spray nozzle. The method can additionally comprise circulating a gas or air within the chamber.

In accordance with another aspect, a stent coating apparatus is provided. Some embodiments comprise an elongated member having multiple stent coupling elements longitudinally positioned in series along the body of the elongated member such that each stent coupling element is adapted to secure stents during the process of applying a coating substance to the stent. The coupling element can comprise a first member to contact one end of the stent and a second or locking member to contact an opposing end of the stent. The stent can be releasably secured between the first and second member. A motor is coupled to one end of the elongated member for rotating all of the stents about a common longitudinal axis of the stents. Alternatively, there can be multiple axis or rotation.

DETAILED DESCRIPTION

Figure 1:
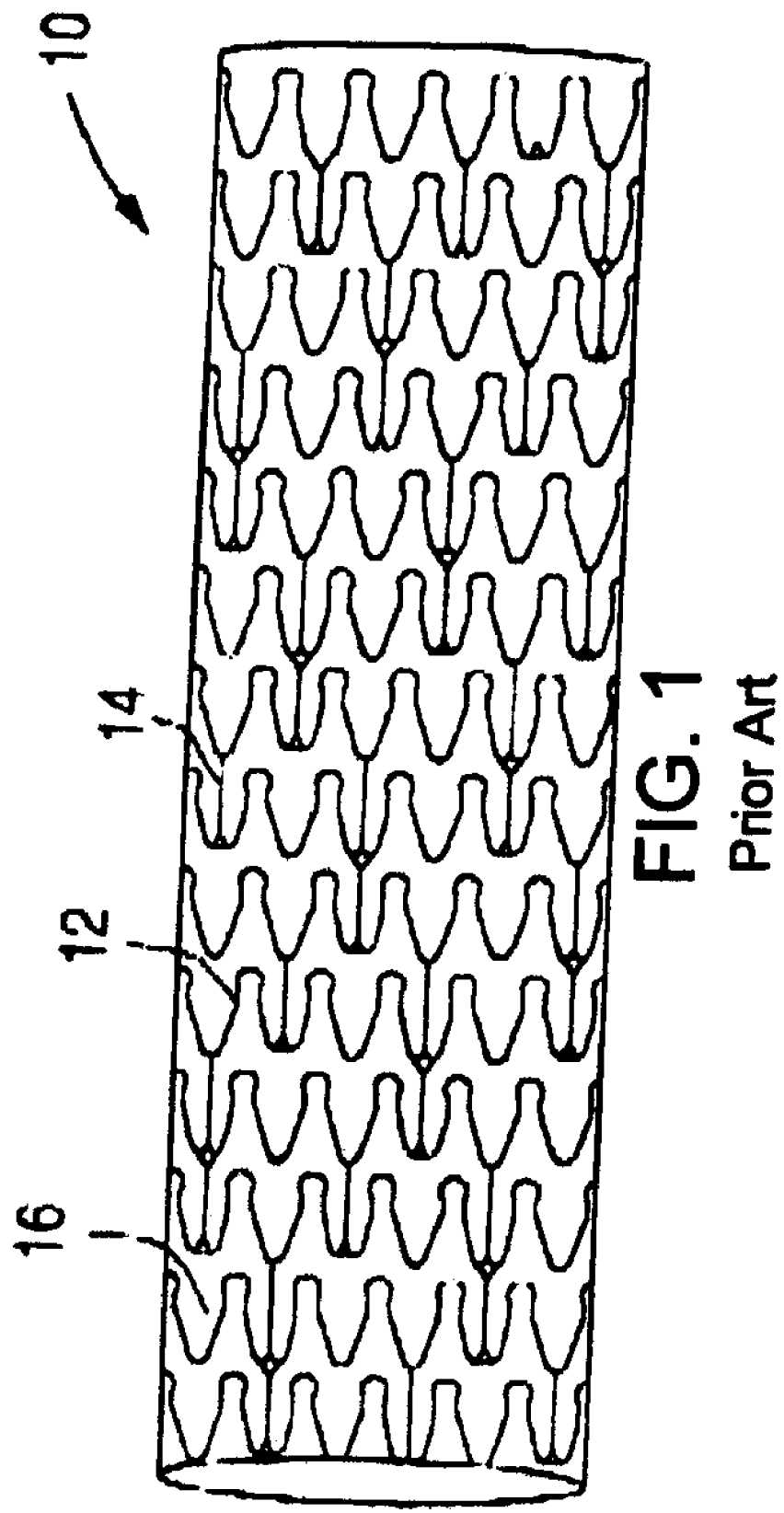
FIG. 1 illustrates a conventional stent.
Figure 2:
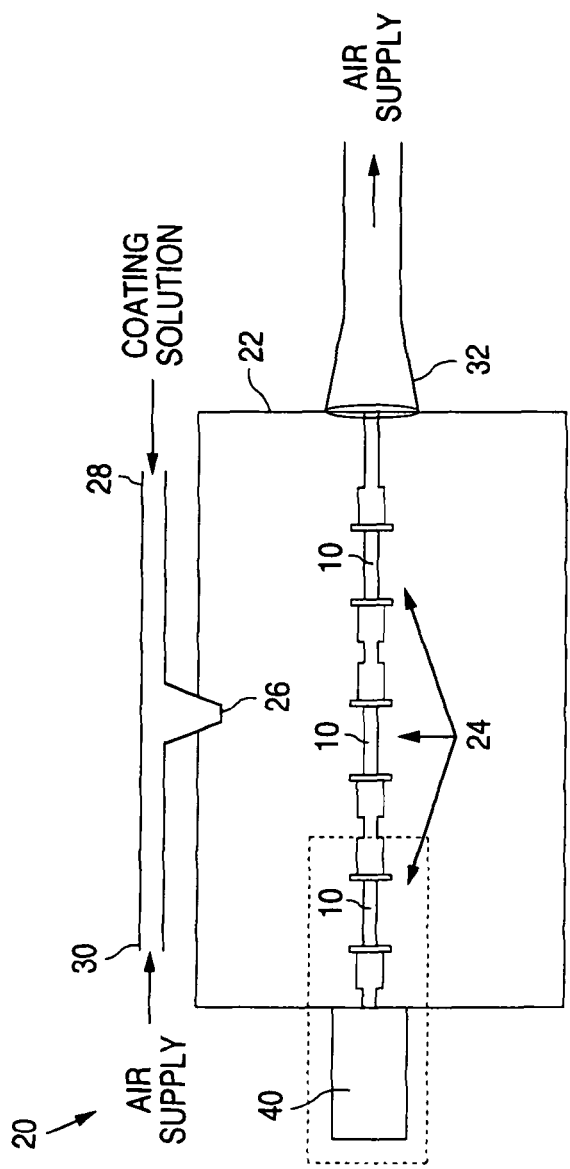
FIG. 2 illustrates a coating apparatus according to an embodiment of the invention.

FIG. 2 illustrates a stent coating apparatus 20 according to an embodiment of the invention. Apparatus 20 comprises a coating chamber 22 that can be impervious to light. Impervious to light is defined as significantly inhibiting or completely preventing light having any harmful frequency and wavelength from penetrating into chamber 22. More particularly, in one embodiment, ultraviolet, visible, and/or infrared light should be inhibited or prevented from penetrating into chamber 22.

Figure 4:
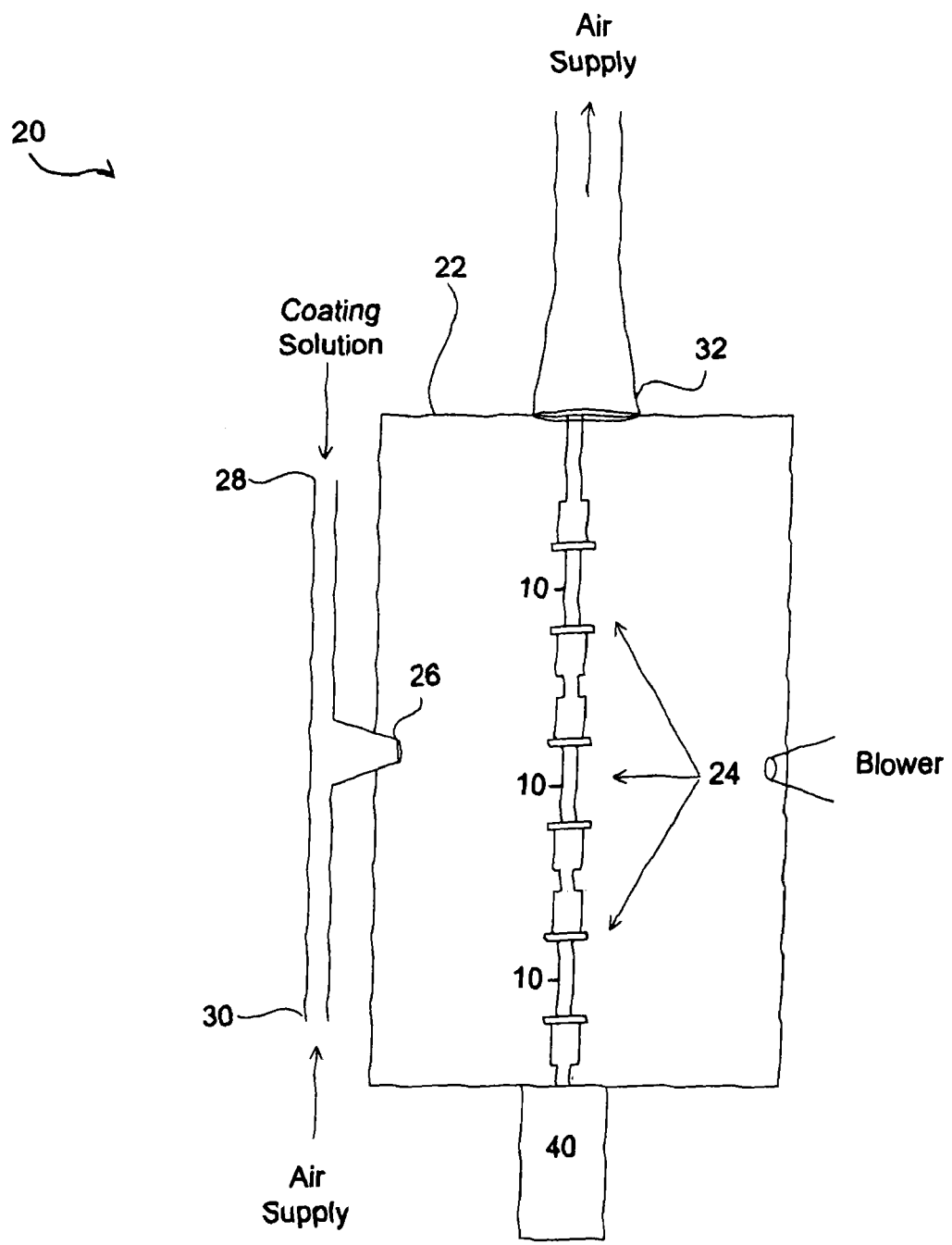
FIG. 4 illustrates a coating apparatus according to another embodiment of the invention.

Apparatus 20 includes a plurality of stent mandrel fixtures or supports 24 for holding and rotating stents 10 during application of the coating composition. While the embodiment of FIG. 2 shows three fixtures or supports 24 positioned in series, any number of fixtures or supports 24 can be used. Additionally, fixtures or supports 24 can be positioned in a parallel configuration with respect to one another. Fixtures 24 may be positioned either in the horizontal (FIG. 2) or vertical plane (FIG. 4) within apparatus 20.

As clearly illustrated in FIG. 2, stent fixtures or supports 24 are positioned with respect to one another in an adjacent serial configuration such that one end of a stent support extends from an end of the adjacent stent support. The stent fixtures 24 are aligned such that the stents 10 share a common axis of rotation along the longitudinal body of the stents 10. In some embodiments, the stent fixtures 24 can be off-set such that the axis of rotation of the stents 10 is off-set as well. The series of supports 24 can be made from one piece or can be individual units coupled or connected to one another. In some embodiments, collectively, the supports 24 can be a single elongated member having stent connecting elements or coupling means spaced an intervals along the elongated piece. In some embodiments, the supports 24 can be disconnectably coupled to one another such that any number of supports 24 can be communicatively aligned in series. A motor 40 can be coupled to one of or a first in the series of the stent supports 24 such that the rotation of the first stent support can allow for the rotation of the remaining stent supports 24. In this embodiment, all the stents 10 have the same rotational speed (or rpm) during the coating process as each support 24 torques the adjacent support down the line. The motor 40 can rotate the stent during the application of the coating process, during the drying process, or anytime during the manufacturing process.

In alternative embodiments, a bearing or other means known in the art can be used to couple any two of the stent supports 24. In other words, the bearing or coupling means can be used to connect adjacent supports 24. The bearing or coupling will provide for a different rotational speed for each stent. For example, in FIG. 2, a bearing can be provided between the left stent and the middle stent supports 24. Accordingly, the left stent 10 will rotate at a different speed than the middle and right stents. If another bearing was using between the middle stent support and the right stent support, then each stent can rotate at a different speed.

Apparatus 20 additionally includes a spray nozzle assembly 26 penetrating inside chamber 22. Nozzle assembly 26 can be in fluid communication with one or multiple coating composition sources via an inlet 28. Multiple composition sources allow a variety of coating compositions to be applied to stents 10, for example in a time delay or time synchronized fashion. Nozzle assembly 26 can also be coupled to a convection oven or a blower (not shown) via an inlet 30 for application of warm (e.g., above room temperature) or cold (e.g., below room temperature) gas, such as air, to the composition and/or stents 10. In one embodiment, nozzle assembly 26 is capable of generating atomized particles of about 20-30 µm in size. The particle size should not be too small because it may lead to drying rather than to spray coating. Due to Joule-Thompson expansion at nozzle assembly's 26 outlet, the coating composition may cool, leading to precipitation of the polymer. Accordingly, when applying coating compositions that precipitate out, warm air from the convection oven via inlet 30 may be used during the coating application to heat the composition to prevent precipitation.

In some embodiments, other types of applicators can also be used for depositing a coating substance. In some embodiments, the applicator can include an ink-jet dispenser.

In an embodiment of the invention, after a coating process has been completed, warm air from the convection oven may be passed over stents 10 to dry the coating. The convection air can then exit chamber 22 via an outlet 32.

Figure 3:
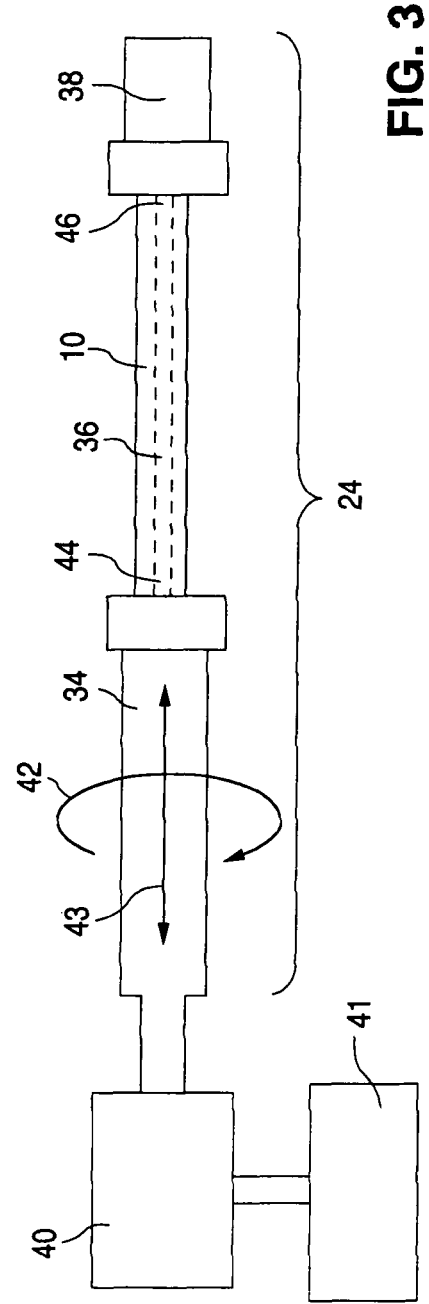
FIG. 3 illustrates one embodiment of a stent mandrel fixture of the apparatus of FIG. 2.

FIG. 3 illustrates fixture 24 in accordance with an embodiment of the invention. As illustrated by the dotted lines, this is a section taken from FIG. 2. Fixture 24 for supporting stent 10 is illustrated to include a support member 34, a mandrel 36, and a lock member 38. Support member 34, mandrel 36, and lock member 38 are one form of connecting elements or coupling means that can be used although others types can be contemplated by one skilled in the art. Support member 34 can connect to a motor 40 so as to provide rotational motion about the longitudinal axis of stent 10, as depicted by arrow 42, during the coating process. Another motor 41 can also be provided for moving support members 24 in a linear direction, back and forth, traversing the nozzle 26. Each stent should be able to completely traverse back and forth, passing the nozzle completely.

Support member 34 can also include a bore (not shown) for receiving a first end 44 of mandrel 36. First end 44 of mandrel 36 can be threaded to screw into the bore or, alternatively, can be retained within the bore by a friction fit. The bore should be deep enough so as to allow mandrel 36 to securely mate with support member 34. The depth of the bore can also be over-extended so as to allow a significant length of mandrel 36 to penetrate or screw into the bore. This would allow the length of mandrel 36 to be adjusted to accommodate stents of various sizes.

The outer diameter of mandrel 36 can be smaller than the inner diameter of stent 10 so as to prevent the outer surface of mandrel 36 from making contact with the inner surface of stent 10. A sufficient clearance between the outer surface of mandrel 36 and the inner surface of stent 10 should be provided to prevent mandrel 36 from obstructing the pattern of the stent body during the coating process. By way of example, the outer diameter of mandrel 36 can be from about 0.010 inches (0.254 mm) to about 0.017 inches (0.432 mm) when stent 10 has an inner diameter of between about 0.025 inches (0.635 mm) and about 0.035 inches (0.889 mm).

A second end 46 of mandrel 36 can be permanently affixed to lock member 38 if first end 44 is disengageable from support member 34. Alternatively, in accordance with another embodiment, mandrel 36 can have a threaded second end 46 for screwing into a bore (not shown) of lock member 38. This bore can be of any suitable depth that would allow lock member 38 to be incrementally moved closer to support member 34. Fixture 24 allows stents 10 of any length to be securely pinched between support and lock members 34 and 38. In accordance with yet another embodiment, a non-threaded second end 46 and bore combination can be employed such that second end 46 can be press-fitted or friction-fitted within the bore to prevent movement of stent 10 on stent mandrel fixture 24.

The coating composition can include a solvent, a polymer dissolved in the solvent and optionally a wetting fluid added thereto. The composition can also include therapeutic substances or active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

A wetting fluid can be used to enhance the wetting of the composition or to increase the capillary permeation of the composition. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of wetting fluid include tetrahydrofuran (THF), dimethylformamide (DMF), 1-butanol, and n-butyl acetate.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chlorbmethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating stents, comprising:
   placing stents in a coating chamber housing a first stent support and a second stent support for supporting stents, the first and second stent supports positioned with respect to one another in an adjacent serial configuration such that one end of the first stent support extends from an end of the adjacent second stent support;
   using a motor coupled to the first stent support to rotate the first stent support such that the rotation of the first stent support causes the second stent support to rotate; and
   applying a coating composition on the stents by a coating applicator.

2. The method of claim 1, wherein the first stent support and second stent support rotate at the same rotational speed.

3. The method of claim 1, wherein the first stent support is coupled to the second stent support by a means for causing the first stent support to rotate at a different rotational speed than the second stent support.

4. The method of claim 1, additionally using a blower to blow warm or cold gas onto the stents.

5. The method of claim 1, wherein the stents are positioned vertically in the coating chamber.

6. The method of claim 1, wherein the stents are positioned horizontally in the coating chamber.

7. The method of claim 1, additionally comprising using a second motor for traversing the stents linearly passed the coating applicator.

8. The method of claim 1, wherein the coating applicator is a spray nozzle.

9. The method claim 1, wherein the coating applicator is capable of being in communication with multiple coating composition sources for the application of different coating compositions.

10. The method of claim 1, additionally comprising circulating a gas or air within the chamber.

* * * * *